United States Patent
Bessette et al.

(12)

(10) Patent No.: US 6,531,163 B1
(45) Date of Patent: Mar. 11, 2003

(54) PESTICIDAL COMPOSITIONS CONTAINING PEPPERMINT OIL

(75) Inventors: Steven M. Bessette, Brentwood, TN (US); Essam E. Enan, Franklin, TN (US)

(73) Assignee: Ecosmart Technologies, Inc., Franklin, TN (US)

( * ) Notice: Subject to any disclaimer, the term of this patent is extended or adjusted under 35 U.S.C. 154(b) by 0 days.

(21) Appl. No.: 09/604,397

(22) Filed: Jun. 27, 2000

Related U.S. Application Data
(60) Provisional application No. 60/140,845, filed on Jun. 28, 1999.

(51) Int. Cl.[7] ............................................. A01N 65/00
(52) U.S. Cl. ....................................... 424/747; 424/725
(58) Field of Search ................................ 424/725, 747, 424/757, 405, 409

(56) References Cited

U.S. PATENT DOCUMENTS

| | | | |
|---|---|---|---|
| 4,053,595 A | * 10/1977 | Zeck et al. | ................. 424/216 |
| 4,759,930 A | 7/1988 | Granirer et al. | |
| 5,403,587 A | 4/1995 | McCue et al. | |

FOREIGN PATENT DOCUMENTS

| | | |
|---|---|---|
| EP | 0945966 | 9/1999 |
| JP | 03127702 | 5/1991 |
| JP | 06107505 | 4/1994 |
| JP | 406107505 A | * 4/1994 |
| WO | WO98/30124 | 7/1998 |
| WO | WO9952359 | 10/1999 |

OTHER PUBLICATIONS

Ngoh, Shay, et al., "Insecticidal and Repellent Properties of Nine Volatile Constituents of Essential Oils against the American Cockroach, *Periplaneta americana* (L.)", Pestic-.Sci., (1998) 54(3), 261–268.
Hori, Masatoshi, "Repellency of Rosemary Oil Aganinst *Myzus persicae* in a Laboratory and in the Screehouse", J.Chemical Ecology, vol. 24, No. 9, 1998, pp 1425–1433.
Database WPI, Derwent Publications, Ltd., London, GB, "Insecticial Composition Contains Plant Oil and/or Terpene Oil to Improve Insecticidal Effect".
King, W.V., "Chemicals Evaluated as Insecticides and Repellents at Orlando, Fla.", Agric. Handbook, 1954, p. 1–17.
Rompps Chemie Lexikon, "Rosmarinol", 1992, Geoge__ Thieme–Verlang, Stuttgart, Germany.
Coats, Joel et al., "Toxicity and Neurotoxic Effects of Monoterpeniods in Insects and Earthworms", ACS. Symp.Ser. (1991), 449 (Nat. Occuring Pest Bioregul.) 305–16.
Karr, L.L. et al. "Effects of Four Monoterpeniods on the Growht and Reproduction of the German Cockroach", J. Pestic. Science, vol. 85, No. 2, 1992, pp. 424–429.
Database WPI, Aug. 9, 190, Derwent Publications Ltd London, "Cockroach Repellent Comprising a Menthol and Pyrethrum, Pyrethrin, Para–Dichlorbenzene, Naphthalene and Camphor".
Inazuka, S., "New Methods of Evaluation for Cockroach Repellants and Repellency of Essential Oils Against German Cockroach (*Blatella germanica*)", J. Pestic. Science, vol. 7, 1982, pp. 133–134.
Inazuka, S., "Cockroaches Repellents Contained in Oils Japanese Mint and Scotch Spearmint", J. Pestic. Science, vol. 7, 1982, pp. 145–154.
Pesticide & Toxic Chemical News, PROMPT Full Text article, 1994, pp. 1–3.*
Vartak et al. Comparative Repellaent Properties of Certain Chemicals Against Mosquitoes, House Flies and Cockroaches Using Modified Techniques; J. Com. Dis., 26 (3): 156–160, 1994.*
Kohn ed. et al. Mechanism of Pesticide Action; 1974, American Chemical Society, p. 39.*

* cited by examiner

*Primary Examiner*—Jon P. Weber
*Assistant Examiner*—Patricia Patten
(74) *Attorney, Agent, or Firm*—McDermott, Will & Emery

(57) ABSTRACT

Pesticidal compositions for the control of household pests, such as cockroaches and ants contain peppermint oil (or cornmint oil), optionally blended with one or more plant essential oils. The present invention is also directed to synergistic pesticidal compositions containing peppermint oil optionally blended with at least one plant essential oils. Further, the present invention is directed to a method for controlling household pests, such as cockroaches and ants, by applying a pesticidally-effective amount of the inventive pesticidal composition to a locus where pest control is desired.

26 Claims, No Drawings

PESTICIDAL COMPOSITIONS CONTAINING PEPPERMINT OIL

CROSS REFERENCE TO RELATED APPLICATION

This application claims the benefit of U.S. Provisional Application Ser. No. 60/140,845, filed Jun. 28, 1999, the entire disclosure of which is incorporated herein by reference.

FIELD OF THE INVENTION

The present invention relates, in general, to pesticidal compositions containing peppermint oil against household pests, including cockroaches and ants. In one aspect, the present invention relates to pesticidal compositions comprising peppermint oil, optionally blended with one or more plant essential oils and/or derivatives thereof, to be used as a contact pesticide against household pests. In another aspect, the present invention relates to the use of new technology to achieve synergistic activity between or among peppermint oil and at least one member selected from the group consisting of eugenol, phenethyl propionate, and benzyl alcohol. The present invention also relates to synergistic compositions comprising peppermint oil in combination with metabolic detoxication inhibitors, piperonyl butoxide (PBO) and signal transduction modulators, such as members of the family of tyrosine kinase inhibitors (e.g. genistein). The present invention also relates to pesticidally effective ratios between or among the constituents of the above inventive blends and the proper delivery system for each blend. In a further aspect, the present invention relates to a method for controlling household pests, including, without limitation, cockroaches and ants, by the application of pesticidally effective amounts of the inventive pesticidal compositions to a location where pest control is desired.

BACKGROUND OF THE INVENTION

Pests (invertebrates, insects, arachnids, larvae thereof, etc.) are annoying to humans for a myriad of reasons. They have annually cost humans billions of dollars in crop losses and in the expense of keeping them under control. For example, the losses caused by pests in agricultural environments include decreased crop yield, reduced crop quality, and increased harvesting costs. In household scenarios, insect pests may act as vectors for diseases and allergic matter.

Over the years, synthetic chemical pesticides have provided an effective means of pest control. For example, one approach teaches the use of complex, organic insecticides, such as disclosed in U.S. Pat. Nos. 4,376,784 and 4,308,279. Other approaches employ absorbent organic polymers for widespread dehydration of the insects. See, U.S. Pat. Nos. 4,985,251; 4,983,390; 4,818,534; and 4,983,389. Use of inorganic salts as components of pesticides has also been tried, as disclosed in U.S. Pat. Nos. 2,423,284 and 4,948,013, European Patent Application No. 462 347, Chemical Abstracts 119(5):43357q (1993) and Farm Chemicals Handbook, page c102 (1987).

However, it has become increasingly apparent that the widespread use of synthetic chemical pesticides has caused detrimental environmental effects that are harmful to humans and other animals. For instance, the public has become concerned about the amount of residual chemicals that persist in food, ground water and the environment, and that are toxic, carcinogenic or otherwise incompatible to humans, domestic animals and/or fish. Moreover, some target pests have even shown an ability to develop resistance to many commonly used synthetic chemical pesticides. In recent times, regulatory guidelines have encouraged a search for potentially less dangerous pesticidal compositions via stringent restrictions on the use of certain synthetic pesticides. As a result, elimination of effective pesticides from the market has limited economical and effective options for controlling pests. As an alternative, botanical pesticides are of great interest because they are natural pesticides, i.e., toxicants derived from plants that are safe to humans and the environment.

Accordingly, there is a great need for novel pesticidal compositions that contain no pyrethrum, synthetic pyrethroids, chlorinated hydrocarbons, organo phosphates, carbamates, and the like, that may be used against household pests, including, without limitation, cockroaches and ants. In addition, there is a need for a method of treating the household to kill and repel insect pests.

SUMMARY OF THE INVENTION

A primary object of the present invention is to provide novel pesticidal compositions for use against household pests, including cockroaches and ants.

Another object of the invention is to provide novel pesticidal compositions containing peppermint oil (including cornmint oil), optionally blended with one or more natural or synthetic plant essential oils compounds and/or derivatives thereof, as a contact and repellent pesticide in the household.

It is also an object of the present invention to provide a method of treating a locus where pest control is desired.

It is also an object of the present invention to provide a pesticidal composition and method for mechanically and neurally controlling household pests.

It is a further object to provide a safe, non-toxic pesticidal composition and method that will not harm mammals or the environment.

It is still another object to provide a pesticidal composition and method that has a pleasant scent or is unscented, and that can be applied without burdensome safety precautions.

It is still another object to provide a pesticidal composition and method as described above which can be inexpensively produced or employed.

It is yet another object of the invention to provide a pesticidal composition and method to which pests cannot build resistance.

The above and other objects are accomplished by the present invention which is directed to pesticidal compositions comprising peppermint oil (including cornmint oil), optionally blended with a natural or synthetic plant essential oil compound and/or derivative thereof, in admixture with a suitable carrier. In addition, the present invention is directed to a method for controlling household pests by applying a pesticidally-effective amount of the inventive pesticidal compositions disclosed herein to a location where pest control is desired.

Additional objects and attendant advantages of the present invention will be set forth, in part, in the description that follows, or may be learned from practicing or using the present invention. The objects and advantages may be realized and attained by means of the instrumentalities and combinations particularly recited in the appended claims. It is to be understood that the foregoing general description and the following detailed description are exemplary and explanatory only and are not to be viewed as being restrictive of the invention, as claimed.

DETAILED DESCRIPTION OF PREFERRED EMBODIMENTS

All patents, patent applications and literatures cited in this description are incorporated herein by reference in their entirety.

In one embodiment, the present invention provides a pesticidal composition comprising peppermint oil and/or cornmint oil, in admixture with a suitable carrier, optionally with a suitable surface active agent, and optionally blended with one or more natural or synthetic plant essential oil compounds and/or derivatives thereof, including racemic mixtures, enantiomers, diastereomers, hydrates, salts, solvates and metabolites, etc. As used herein, the term "plant essential oil" or "plant essential oil compound" (which shall include derivatives thereof) generally refers to a monocyclic, carbocyclic ring structure having six-members and substituted by at least one oxygenated or hydroxyl functional moiety. Examples of plant essential oils encompassed within the present invention, include, but are not limited to, members selected from the group consisting of aldehyde C16 (pure), α-terpineol, amyl cinnamic aldehyde, amyl salicylate, anisic aldehyde, benzyl alcohol, benzyl acetate, cinnamaldehyde, cinnamic alcohol, carvacrol, carveol, citral, citronellal, citronellol, p-cymene, diethyl phthalate, dimethyl salicylate, dipropylene glycol, eucalyptol (cineole), eugenol, iso-eugenol, galaxolide, geraniol, guaiacol, ionone, menthol, menthyl salicylate, methyl anthranilate, methyl ionone, methyl salicylate, a-phellandrene, pennyroyal oil, perillaldehyde, 1- or 2-phenyl ethyl alcohol, 1- or 2-phenyl ethyl propionate, piperonal, piperonyl acetate, piperonyl alcohol, D-pulegone, terpinen-4-ol, terpinyl acetate, 4-tert butylcyclohexyl acetate, thyme oil, thymol, metabolites of trans-anethole, vanillin, ethyl vanillin, and the like. As these plant essential oil compounds are known and used for other non-pesticidal uses, they may be prepared by a skilled artisan by employing known methods or obtained from commercially available sources.

For example, in a preferred embodiment, the present invention is directed to a pesticidal composition for controlling cockroaches and ants comprising a mixture of plant essential oils which include 40% peppermint oil, and 40% benzyl alcohol with a suitable solvent carrier. Efficacy data shows that this embodiment is highly effective, i.e. exhibited fast knockdown and mortality against cockroaches.

It will be appreciated by the skilled artisan that the pesticidal compositions of the present invention unexpectedly exhibit excellent pesticidal activities using one or more U.S. F.D.A. approved plant essential oils, in lieu of conventional pesticides which are not safe for use in households and other sensitive areas. Without wishing to be bound by the following theories, it is believed that plant essential oils attack a pest's nervous system or may act as Phase I and/or Phase II drug metabolizing enzyme inhibitors. Alternatively, the plant essential oils may act via an alternative mode of action. The plant essential oils may even act as agonists or antagonists against the octopamine/octopamine receptors system that are distinct to invertebrates. In any event, the net effect of the toxicity and action of the inventive composition disclosed herein is heretofore unknown and unexpectedly superior.

Use of pesticidal compositions of the present invention generally results in fast knockdown and 100% mortality on contact. As such, they are advantageously employed as pesticidal agents in uses such as, without limitation, households, agriculture, organic farming, professional pest control, pet bedding, foliage application, underwater or submerged application, solid treatment, soil incorporation application, seedling box treatment, stalk injection and planting treatment, ornamentals, termites, mosquitoes, fire ants, head lice, dust mites, etc.

With respect to soil, the pesticidal compositions resist weathering which includes wash-off caused by rain, decomposition by ultra-violet light, oxidation, or hydrolysis in the presence of moisture or, at least such decomposition, oxidation and hydrolysis as would materially decrease the desirable pesticidal characteristic of the pesticidal compositions or impart undesirable characteristics to the pesticidal compositions. The pesticidal compositions are so chemically inert that they are compatible with substantially any other constituents of pest control, and they may be used in the soil, upon the seeds, or the roots of plants without injuring either the seeds or roots of plants. They may also be used in combination with other pesticidally active compounds.

The term "carrier" as used herein means an inert or fluid material, which may be inorganic or organic and of synthetic or natural origin, with which the active compound is mixed or formulated to facilitate its application to the container or carton or other object to be treated, or its storage, transport and/or handling. In general, any of the materials customarily employed in formulating pesticides, herbicides, or fungicides, are suitable. The inventive pesticidal compositions of the present invention may be employed alone or in the form of mixtures with such solid and/or liquid dispersible carrier vehicles and/or other known compatible active agents such as other pesticides, or acaricides, nematicides, fungicides, bactericides, rodenticides, herbicides, fertilizers, growth-regulating agents, etc., if desired, or in the form of particular dosage preparations for specific application made therefrom, such as solutions, emulsions, suspensions, powders, pastes, and granules which are thus ready for use. The pesticidal compositions of the present invention can be formulated or mixed with, if desired, conventional inert pesticide diluents or extenders of the type usable in conventional pesticide formulations or compositions, e.g. conventional pesticide dispersible carrier vehicles such as gases, solutions, emulsions, suspensions, emulsifiable concentrates, spray powders, pastes, soluble powders, dusting agents, granules, foams, pastes, tablets, aerosols, natural and synthetic materials impregnated with active compounds, microcapsules, coating compositions for use on seeds, and formulations used with burning equipment, such as fumigating cartridges, fumigating cans and fumigating coils, as well as ULV cold mist and warm mist formulations, etc.

Formulations containing the pesticidal compositions of the present invention may be prepared in any known manner, for instance by extending the pesticidal compositions with conventional pesticide dispersible liquid diluent carriers and/or dispersible solid carriers optionally with the use of carrier vehicle assistants, e.g. conventional pesticide surface-active agents, including emulsifying agents and/or dispersing agents, whereby, for example, in the case where water is used as diluent, organic solvents may be added as auxiliary solvents. Suitable liquid diluents or carriers include water, petroleum distillates, or other liquid carriers with or without surface active agents. The choice of dispersing and emulsifying agents and the amount employed is dictated by the nature of the composition and the ability of the agent to facilitate the dispersion of the pesticidal compositions of the present invention. Non-ionic, anionic, amphoteric, or cationic dispersing and emulsifying agents may be employed, for example, the condensation products of alkylene oxides with phenol and organic acids, alkyl aryl sulfonates, complex ether alcohols, quarternary ammonium compounds, and the like.

Liquid concentrates may be prepared by dissolving a composition of the present invention with a solvent and dispersing the pesticidal compositions of the present inventions in water with the acid of suitable surface active emulsifying and dispersing agents. Examples of conventional carrier vehicles for this purpose include, but are not limited to, aerosol propellants which are gaseous at normal temperatures and pressures, such as Freon; inert dispersible liquid diluent carriers, including inert organic solvents, such as aromatic hydrocarbons (e.g. benzene, toluene, xylene, alkyl naphthalenes, etc.), halogenated especially chlorinated, aromatic hydrocarbons (e.g. chloro-benzenes, etc.), cycloalkanes, (e.g. cyclohexane, etc.). paraffins (e.g. petroleum or mineral oil fractions), chlorinated aliphatic hydrocarbons (e.g. methylene chloride, chloroethylenes, etc.), alcohols (e.g. methanol, ethanol, propanol, butanol, glycol, etc.) as well as ethers and esters thereof (e.g. glycol monomethyl ether, etc.), amines (e.g. ethanolamine, etc.), amides (e.g. dimethyl formamide etc.) sulfoxides (e.g. dimethyl sulfoxide, etc.), acetonitrile, ketones (e.g. acetone, methyl ethyl ketone, methyl isobutyl ketone, cyclohexanone, etc.), and/or water; as well as inert dispersible finely divided solid carriers such as ground natural minerals (e.g. kaolins, clays, vermiculite, alumina, silica, chalk, i.e. calcium carbonate, talc, attapulgite, montmorillonite, kieselguhr, etc.) and ground synthetic minerals (e.g. highly dispersed silicic acid, silicates, e.g. alkali silicates, etc.).

Surface-active agents, i.e., conventional carrier vehicle assistants, that may be employed with the present invention include, without limitation, emulsifying agents, such as non-ionic and/or anionic emulsifying agents (e.g. polyethylene oxide esters of fatty acids, polyethylene oxide ethers of fatty alcohols, alkyl sulfates, alkyl sulfonates, aryl sulfonates, albumin hydrolyzates, etc. and especially alkyl arylpolyglycol ethers, magnesium stearate, sodium oleate, etc.); and/or dispersing agents such as lignin, sulfite waste liquors, methyl cellulose, etc.

In the preparation of wettable powders, dust or granulated formulations, the active ingredient is dispersed in and on an appropriately divided carrier. In the formulation of the wettable powders the aforementioned dispersing agents as well as lignosulfonates can be included. Dusts are admixtures of the compositions with finely divided solids such as talc, attapulgite clay, kieselguhr, pyrophyllite, chalk, diatomaceous earth, vermiculite, calcium phosphates, calcium and magnesium carbonates, sulfur, flours, and other organic and inorganic solids which acts carriers for the pesticide. These finely divided solids preferably have an average particle size of less than about 50 microns. A typical dust formulation useful for controlling insects contains 1 part of pesticidal composition and 99 parts of diatomaceous earth or vermiculite. Granules may comprise porous or nonporous particles. The granule particles are relatively large, a diameter of about 400–2500 microns typically. The particles are either impregnated or coated with the inventive pesticidal compositions from solution. Granules generally contain 0.05–15%, preferably 0.5–5%, active ingredient as the pesticidally-effective amount. Thus, the contemplated are formulations with solid carriers or diluents such as bentonite, fullers earth, ground natural minerals, such as kaolins, clays, talc, chalk, quartz, attapulgite, montmorillonite or diatomaceous earth, vermiculite, and ground synthetic minerals, such as highly-dispersed silicic acid, alumina and silicates, crushed and fractionated natural rocks such as calcite, marble, pumice, sepiolite and dolomite, as well as synthetic granules of inorganic and organic meals, and granules of organic materials such as sawdust, coconut shells, corn cobs and tobacco stalks. Adhesives, such as carboxymethyl cellulose, natural and synthetic polymers, (such as gum arabic, polyvinyl alcohol and polyvinyl acetate), and the like, may also be used in the formulations in the form of powders, granules or emulsifiable concentrations.

If desired, colorants such as inorganic pigments, for example, iron oxide, titanium oxide and Prussian Blue, and organic dyestuffs, such as alizarin dyestuffs, azo dyestuffs or metal phthalocyanine dyestuffs, and trace elements, such as salts of iron, manganese, boron, copper, cobalt, molybdenum and zinc may be used.

In commercial applications, the present invention encompasses carrier composition mixtures in which the pesticidal compositions are present in an amount substantially between about 0.01–95% by weight, and preferably 0.5–90% by weight, of the mixture, whereas carrier composition mixtures suitable for direct application or field application generally contemplate those in which the active compound is present in an amount substantially between about 0.0001–10%, preferably 0.01–1%, by weight of the mixture. Thus, the present invention contemplates over-all formulations that comprise mixtures of a conventional dispersible carrier vehicle such as (1) a dispersible inert finely divided carrier solid, and/or (2) a dispersible carrier liquid such as an inert organic solvent and/or water, preferably including a surface-active effective amount of a carrier vehicle assistant, e.g. a surface-active agent, such as an emulsifying agent and/or a dispersing agent, and an amount of the active compound which is effective for the purpose in question and which is generally between about 0.0001–95%, and preferably 0.01–95%, by weight of the mixture.

The pesticidal compositions can also be used in accordance with so-called ultra-low-volume process, i.e. by applying such compounds or by applying a liquid composition containing the same, via very effective atomizing equipment, in finely divided form, e.g. average particle diameter of from 50–100 microns, or even less, i.e. mist form, for example by airplane crop spraying techniques. In this process it is possible to use highly concentrated liquid compositions with said liquid carrier vehicles containing from about 20 to 95% by weight of the pesticidal compositions or even the 100% active substances alone, e.g. about 20–100% by weight of the pesticidal compositions. The concentration in the liquid concentrate will usually vary from about 10 to 95 percent by weight and in the solid formulations from about 0.5 to 90 percent by weight.

Furthermore, the present invention encompasses methods for killing, combating or controlling pests, which comprises applying to at least one of correspondingly (a) such pests and (b) the corresponding habitat thereof, i.e. the locus to be protected, e.g. to the household, a correspondingly combative, a pesticidally effective amount, or toxic amount of the particular pesticidal compositions of the invention alone or together with a carrier as noted above. The instant formulations or compositions may be applied in any suitable usual manner, for instance by spraying, atomizing, vaporizing, scattering, dusting, watering, squirting, sprinkling, pouring, fumigating, and the like. The method for controlling household pests such as cockroaches and ants comprises applying the inventive composition, ordinarily in a formulation of one of the aforementioned types, to a locus or area to be protected from the cockroaches and/or ants, such as the household. The compound, of course, is applied in an amount sufficient to effect the desired action. This dosage is dependent upon many factors, including the targeted pest, the carrier employed, the method and conditions of the application, whether the formulation is present at the locus in the form of an aerosol, or as a film, or as discrete particles, the thickness of film or size of particles, and the like. Proper consideration and resolution of these factors to provide the necessary dosage of the active compound at the locus to be protected are within the skill of those versed in the art. In general, however, the effective dosage of the compound of this invention at the locus to be protected—i.e., the dosage with which the pest comes in contact—is of the order of 0.001 to 5.0% based on the total weight of the formulation, though under some circumstances the effective concentration will be as little as 0.0001% or as much as 20%, on the same basis.

The pesticidal compositions and methods of the present invention are effective against different species of household pests and it will be understood that the insects exemplified and evaluated in the working Examples herein is representative of such a wider variety.

The composition and method of the present invention will be further illustrated in the following, non-limiting Examples. The Examples are only illustrative of various preferred embodiments of the present invention and do not limit the claimed invention regarding the materials, conditions, weight ratios, process parameters and the like recited herein.

EXAMPLE 1

Pesticidal Effects of Plant Essential Oils Against the American and German Cockroach Certain plant essential oils and mixtures thereof were evaluated for contact toxicity (topical application and walk-across) against the German and American cockroaches. The plant essential oils were dissolved in an Isopar solvent at a 1:10 ratio by weight of plant essential oil to Isopar. Topical application of the test substance was performed to test the efficacy of peppermint oil and benzyl alcohol against German and American cockroaches. The treated cockroaches were then placed in clean petri dishes and observed for mortality one hour post treatment. In addition, approximately 1 ml of each test substance was applied to Whatman No. 1 filter paper and placed in 9-cm diam. glass petri dishes. German and American cockroaches were then exposed to the petri dishes and observed for mortality one hour post treatment. The test substances included a combination of 40% benzyl alcohol, 40% peppermint oil. All test substances were highly toxic to both German and American cockroaches.

These data suggested that peppermint oil and benzyl alcohol may be used as a safe and effective alternative pesticide for control of household pests, including German and American cockroaches.

EXAMPLE 2

Pesticidal Effects of Peppermint Oil Blends Against German Cockroach, American Cockroach and Red Ants (Harvester)

Based on the above data, a series of experiments were performed to test the insecticidal activity of peppermint oil with other plant essential oils such as eugenol and phenethyl propionate (PEP). In addition, the study aimed to address the synergistic action between peppermint oil and piperonyl butoxide. The synergistic action between peppermint oil and tyrosine kinases inhibitor was also investigated.

A. German Cockroach Study. Three products of peppermint-blends were tested against German cockroach. These three blends are:

1. 10% Peppermint blend which consists of: 10% peppermint oil, 0.5% eugenol, 1.25% PEP, 85% ISOPAR M, 2.5% isopropyl alcohol (IPA), and 20% propellant.
2. 5% peppermint, which consists of 5% peppermint oil, 0.25% eugenol, 0.63% PEP, 91.3% ISOPAR M, 2,5% IPA, and 20% propellant.
3. 4% Benzyl Alcohol (BA), which consists of 0.00% peppermint oil, 5% BA, 0.63% eugenol, 1.6% PEP, 90.3% ISOPAR M, 2.5% IPA, and 20% propellant.

Peppermint oil (100%, P-2663) was used as the primary test active ingredient, while cornmint oil (100%, T-6389) was used as an alternative test active ingredient. One glass jar was treated with 100 mg of either test material. Three German cockroaches were transferred to each jar. Knockdown (KD)/Mortality were recorded over time during continuous exposure.

RESULTS

| Test Chemical | number of insects/test | KD/mortality | time |
|---|---|---|---|
| 10% Peppermint blend | 3 | 3/0 | 1 min |
| | | 3/2 | 3 min |
| | | 1/1 | 120 min |
| 5% Peppermint blend | 3 | 1/0 | 10 sec |
| | | 1/1 | 45 sec |
| | | 1/0 | 90 sec |
| | | 0/1 | 7 min |
| | | 1/1 | 20 min |
| 4% BA | 3 | 1/1 | 30 sec |
| | | 2/0 | 60 sec |
| | | 1/1 | 15 min |
| | | 1/1 | 40 min |
| Peppermint Oil (100%) | 3 | 3/0 | 1 min |
| | | 3/1 | 80 min |
| | | 2/2 | 120 min |
| Cornmint Oil (100%) | 3 | 1/0 | 1 min |
| | | 1/0 | 3 min |
| | | 1/0 | 10 min |
| | | 1/1 | 21 min |
| | | 2/2 | 35 min |

B. American Cockroach Study. Materials similar to the material used for German cockroach were used in this study, except two different concentrations (100 mg and 400 mg) of each blend were used against American cockroach. Three American cockroaches were used in this study.

RESULTS

| Test Chemical | number of insects/test | KD/mortality 100 mg | KD/mortality 400 mg | time |
|---|---|---|---|---|
| 10% peppermint blend | 3 | 0/0 | 3/0 | 3 min |
| | | 0/0 | 3/3 | 5 min |
| | | 0/3 | N/A | 24 hr |
| 5% Peppermint blend | 3 | 0/0 | 0/3 | 5 min |
| | | 0/3 | N/A | 24 hr |

-continued

RESULTS

| Test Chemical | number of insects/test | KD/mortality 100 mg | KD/mortality 400 mg | time |
|---|---|---|---|---|
| 4% BA | 3 | 0/0 | 3/0 | 1 min |
|  |  | 0/0 | 3/3 | 2 min |
|  |  | 0/3 | N/A | 24 hr |

N/A = Not Applicable

These data clearly demonstrate that peppermint oil and blends thereof are highly toxic to cockroaches. The data also show that the German cockroach is more sensitive to the test blends than the American cockroach.

C. Ant (Red Ants/Harvester) Study. Similar materials that were used in the German cockroach study were used in this study, except 1 ml of each blend was applied to one glass petri dish. About 0.7 ml (excess liquid) of liquid was withdrawn from each dish Five ants were used per treatment.

RESULTS

| Test Chemical | number of insects/test | KD/mortality | time |
|---|---|---|---|
| 10% peppermint blend | 5 | 0/1 | 3 min |
|  |  | 0/1 | 8 min |
|  |  | 0/2 | 12 min |
|  |  | 0/1 | 21 min |
| 5% Peppermint blend | 5 | 0/3 | 3 min |
|  |  | 0/2 | 5 min |
| 4% BA | 5 | 0/1 | 1 min |
|  |  | 0/2 | 3 min |
|  |  | 0/2 | 7 min |
| Peppermint Oil (100%) | 5 | 0/1 | 3 min |
|  |  | 0/2 | 4 min |
|  |  | 0/2 | 5 min |
| Cornmint Oil (100%) | 5 | 0/1 | 3 min |
|  |  | 0/1 | 3 min |
|  |  | 0/2 | 8 min |
|  |  | 0/1 | 32 min |

The above data demonstrate the excellent insecticidal action of peppermint oil and cornmint oil against ants. The blends were also effective, but not as fast-acting as the oils by themselves.

EXAMPLE 3

Pesticidal Effects of Peppermint and Cornmint Oil in ISOPAR M

Because of the speed of KD/M that was observed for the peppermint oil and cornmint oil, they were tested at 1% in ISOPAR M as a delivery system, and compared to ISOPAR M alone. Therefore, the same experiment against ants was repeated using 1% peppermint oil and 1% cornmint oil in ISOPAR M without any other additives. Five ants were used per test.

RESULTS

| Test Chemical | number of insects/test | KD/mortality | time |
|---|---|---|---|
| Peppermint oil (1%) | 5 | 0/3 | 4 min |
|  |  | 0/2 | 6 min |

-continued

RESULTS

| Test Chemical | number of insects/test | KD/mortality | time |
|---|---|---|---|
| Cornmint oil (1%) | 5 | 0/1 | 2 min |
|  |  | 0/1 | 3 min |
|  |  | 0/2 | 5 min |
|  |  | 0/1 | 7 min |
| ISOPAR M (100%) | 5 | 0/1 | 2 min |
|  |  | 0/1 | 4 min |
|  |  | 0/1 | 5 min |
|  |  | 0/1 | 10 min |
|  |  | 0/1 | 21 min |

The data clearly demonstrate that Isopar M is an effective delivery system for these plant essential oils.

To determine whether the toxicity against ants that was observed for plant essential oil blends is due to ISOPAR M or the oils themselves, or the mixture of both, peppermint oil only was tested at 10% in acetone to address whether these active ingredients have the property to kill ants or not. All other actives to be tested in mixture in acetone for their toxicity against ants. Similar protocol of petri dishes treatment as described above was adopted. Five ants were used per test materials. It is noted that the final concentration in each dish test is: BA 40 mg; peppermint oil 40 mg (4%) or 20 mg (2%); PEP 10 mg; eugenol 10 mg; valeric anhydride 10 mg (1%), 15%), 20 mg (2%). Modified I-2× is similar to modified I except 2 ml blend in acetone were used per plate. The ants were exposed to the treated plates after complete evaporation of acetone. All plates kept open during the test.

RESULTS

| Test Chemical | number of insects/test | KD/mortality | time |
|---|---|---|---|
| 10% Peppermint blend (in acetone) | 5 | 1/0 | 25 min |
|  |  | 1/0 | 30 min |
|  |  | 1/0 | 40 min |
|  |  | 2/0 | 60 min |
|  |  | 5/5 | 90 min |
| 4% BA | 5 | 3/0 | 15 min |
| 4% peppermint oil |  | 5/2 | 23 min |
| 1% PEP |  | 3/3 | 30 min |
| 1% eugenol |  |  |  |
| (in acetone) |  |  |  |
| 4% BA | 5 | 1/0 | 10 min |
| 4% peppermint oil |  | 2/0 | 12 min |
| 1% PEP |  | 2/0 | 20 min |
| 1% eugenol |  | 5/3 | 25 min |
| 1% valeric anhydride |  | 2/2 | 30 min |
| (in acetone) |  |  |  |
| Modified I |  |  |  |
| 4% BA | 5 | 1/0 | 13 min |
| 2% peppermint oil |  | 1/3 | 18 min |
| 1% PEP |  | 0/1 | 24 min |
| 1.5% eugenol |  | 0/1 | 27 min |
| 2% valeric anhydride |  |  |  |
| (in acetone) |  |  |  |
| Modified I-2X |  |  |  |
| 4% BA | 5 | 0/1 | 4 min |
| 2% peppermint oil |  | 1/1 | 9 min |
| 1% PEP |  | 1/1 | 11 min |
| 1.5% eugenol |  | 0/2 | 17 min |
| 1% valeric anhydride |  |  |  |
| (in acetone) |  |  |  |

The data clearly demonstrate that ISOPAR M is an effective delivery system for these plant essential oils.

48 Hours Residual Activity Against Harvester Ants

| Test Chemical | number of insects/test | KD/mortality | time |
|---|---|---|---|
| ISOPAR M | 3 | 1/0 | 3 min |
| | | 1/1 | 13 min |
| | | 0/2 | 20 min |
| 4% BA | 3 | 3/0 | 15 min |
| | | 5/2 | 23 min |
| | | 3/3 | 30 min |
| 5% Peppermint blend | 3 | 0/1 | 10 min |
| | | 0/2 | 24 min |
| 10% Peppermint blend | 3 | 0/1 | 35 min |
| | | 0/2 | 55 min |
| Modified I (in acetone) | 3 | 3/3 | 35 min |
| Modified I-2X (in acetone) | 3 | 3/3 | 13 min |

The data demonstrate enhanced residual action when ISOPAR M and IPA are used as a delivery system.

EXAMPLE 4

Pesticidal Effects of Synergized Peppermint Oil Blends

Contact (acute) exposure: A blend (Modified II) consisting of 3% BA, 2% peppermint oil, 0.63% PEP, 0.25% eugenol, 4% IPA, 20% propellant, 70.12% ISOPAR M was prepared. Similar treatment conditions as described above were used to address whether the addition of ISOPAR M, IPA and propellant to modified I will increase its efficacy against ants.

-- RESULTS

| | number of insects/test | KD/mortality | time |
|---|---|---|---|
| Modified II (in 70.12% ISOPAR M) | 5 | 0/2 | simultaneously |
| | | 0/1 | 30 sec |
| | | 0/1 | 60 sec |
| | | 0/1 | 8 min |

Thus, the addition of Isopar M, IPA and propellant to Modified I increased its efficacy as judged by the efficacy data for Modified II.

EXAMPLE 5

Pesticidal Effects of Benyzl Alcohol Blend

Based on the above data two new blends that were based on blend II were prepared for testing against ants (harvesters).

| Constituents | Modified II-a | Modified II-b | Modified II |
|---|---|---|---|
| BA | 20.00% | 83.12% | 3.00% |
| PMO | 8.00% | 2.00% | 2.00% |
| PEP | 2.52% | 0.63% | 0.63% |
| Eugenol | 1.00% | 0.25% | 0.25% |
| IPA | 16.00% | 4.00% | 4.00% |
| Isopar M | 40.00% | 10.00% | 70.12% |
| Propellant | 00.00% | 00.00% | 20.00%-- |

RESULTS

| Test blend | number of insects | KD/M | time |
|---|---|---|---|
| Modified II-a | 5 | 0/1 | 5 min |
| | | 0/1 | 6 min |
| | | 0/1 | 8 min |
| | | 0/2 | 10 min |
| Modified II-b | 5 | 0/1 | 5 min |
| | | 0/2 | 6 min |
| | | 0/1 | 7 min |
| | | 0/1 | 12 min |
| BA (100%) | 3 | 0/1 | 30 min |
| | | 0/2 | 40 min |
| Modified II | 5 | 0/2 | simultaneously |
| | | 0/1 | 30 sec |
| | | 0/1 | 60 sec |
| | | 0/1 | 8 min |

Based on these data, it is believed that an advantage of higher concentrations of BA or ISOPAR M is its residual activity.

As can be seen from the above discussion, the pesticidal combinations of active compounds according to the present invention are markedly superior to known pesticidal agents/active compounds conventionally used for control of household pests.

Although illustrative embodiments of the invention have been described in detail, it is to be understood that the present invention is not limited to those precise embodiments, and that various changes and modifications can be effected therein by one skilled in the art without departing from the scope and spirit of the invention as defined by the appended claims.

What is claimed is:

1. A method for controlling cockroaches and ants, which comprises applying to a locus where control is desired a pesticidally-effective amount of a composition comprising, in admixture with an acceptable carrier, peppermint oil and one or more compounds selected from the group consisting of eugenol, phenyl ethyl propionate, and benzyl alcohol.

2. The method of claim 1, wherein the carrier increases residual activity of the composition and is selected from the group consisting of isoparaffinic hydrocarbons, isopropyl alcohol, and benzyl alcohol.

3. A method for controlling cockroaches and ants, which comprises applying to a locus where control is desired a pesticidally-effective amount of a composition comprising, in admixture with an acceptable carrier, peppermint oil and eugenol.

4. The method of claim 3, wherein the carrier is a isoparaffinic hydrocarbon.

5. The method of claim 3, wherein the carrier is isopropyl alcohol.

6. The method of claim 3, wherein the carrier is benzyl alcohol.

7. A method for controlling cockroaches and ants, which comprises applying to a locus where control is desired a pesticidally-effective amount of a composition comprising, in admixture with an acceptable carrier, peppermint oil and phenyl ethyl propionate.

8. The method of claim 7, wherein the carrier is a isoparaffinic hydrocarbon.

9. The method of claim 7, wherein the carrier is isopropyl alcohol.

10. The method of claim 7, wherein the carrier is benzyl alcohol.

11. A method for controlling cockroaches and ants, which comprises applying to a locus where control is desired a pesticidally-effective amount of a composition comprising, in admixture with an acceptable carrier, peppermint oil and benzyl alcohol.

12. The method of claim 11, wherein the carrier is a isoparaffinic hydrocarbon.

13. The method of claim 11, wherein the carrier is isopropyl alcohol.

14. A method for controlling cockroaches and ants, which comprises applying to a locus where control is desired a pesticidally-effective amount of a composition comprising, in admixture with an acceptable carrier, peppermint oil, eugenol and phenyl ethyl propionate.

15. The method of claim 14, wherein the carrier is a isoparaffinic hydrocarbon.

16. The method of claim 14, wherein the carrier is isopropyl alcohol.

17. The method of claim 14, wherein the carrier is or benzyl alcohol.

18. A method for controlling cockroaches and ants, which comprises applying to a locus where control is desired a pesticidally-effective amount of a composition comprising, in admixture with an acceptable carrier, peppermint oil, eugenol and benzyl alcohol wherein said carrier is not benzyl alcohol.

19. The method of claim 18, wherein the carrier is a isoparaffinic hydrocarbon.

20. The method of claim 18, wherein the carrier is isopropyl alcohol.

21. A method for controlling cockroaches and ants, which comprises applying to a locus where control is desired a pesticidally-effective amount of a composition comprising, in admixture with an acceptable carrier, peppermint oil, phenyl ethyl propionate and benzyl alcohol wherein said carrier is not benzyl alcohol.

22. The method of claim 21, wherein the carrier is a isoparaffinic hydrocarbon.

23. The method of claim 21, wherein the carrier is isopropyl alcohol.

24. A method for controlling cockroaches and ants, which comprises applying to a locus where control is desired a pesticidally-effective amount of a composition comprising, in admixture with an acceptable carrier, peppermint oil, eugenol, phenyl ethyl propionate, and benzyl alcohol wherein said carrier is not benzyl alcohol.

25. The method of claim 24, wherein the carrier is a isoparaffinic hydrocarbon.

26. The method of claim 24, wherein the carrier is isopropyl alcohol. Based on the above data two new blends that were based on blend II were prepared for testing against ants (harvesters). Constituents Modified II-a Modified 11-b Modified II BA 20.00% 83.12% 3.00% PMO 8.00% 2.00% 2.00% PEP 2.52% 0.63% 0.63% Eugenol 1.00% 0.25% 0.25% 3[PA 16.00% 4.00% 4.00% Isopar M 40.00% 10.00% 70.12% Propellant 00.00% 00.00% 20.00%

* * * * *

UNITED STATES PATENT AND TRADEMARK OFFICE
CERTIFICATE OF CORRECTION

PATENT NO. : 6,531,163 B1
DATED : March 11, 2003
INVENTOR(S) : Steven M. Bessette et al.

It is certified that error appears in the above-identified patent and that said Letters Patent is hereby corrected as shown below:

Column 13,
Line 19, after "is" delete "or".
Line 25, after "benzyl alcohol" insert -- , --.

Column 14,
Lines 5 and 15, after "benzyl alcohol" insert -- , --.
Line 20, after "isopropyl alcohol." delete "Based on the above data two blends that were based on blend II were prepared for testing against ants (harvesters). Constituents Modified II-a Modified 11-b Modified II BA 20.00% 83.12% 3.00% PMO 8.00% 2.00% 2.00% PEP 2.52% 0.63% 0.63% Eugenol 1.00% 0.25% 0.25% 3[PA 16.00% 4.00% 4.00% Isopar M 40.00% 10.00% 70.12% Propellant 00.00% 00.00% 20.00%".

Signed and Sealed this

Twelfth Day of October, 2004

JON W. DUDAS
*Director of the United States Patent and Trademark Office*